(12) United States Patent
Eric et al.

(10) Patent No.: US 12,337,296 B2
(45) Date of Patent: Jun. 24, 2025

(54) DETERGENT-MIXED DRY HYDROGEL PARTICLE AND CONCENTRATION AND SPECIFIC ACTIVITY ENHANCEMENT OF MACROMOLECULE

(71) Applicant: AMOUNT BIOTECHNOLOGY INC., Quanzhou (CN)

(72) Inventors: Zhijian Eric, Hangzhou (CN); Min Luo, Hangzhou (CN); Changqing Lv, Hangzhou (CN)

(73) Assignee: AMOUNT BIOTECHNOLOGY INC., Quanzhou (CN)

( * ) Notice: Subject to any disclaimer, the term of this patent is extended or adjusted under 35 U.S.C. 154(b) by 1044 days.

(21) Appl. No.: 17/298,007

(22) PCT Filed: Nov. 22, 2019

(86) PCT No.: PCT/CN2019/120118
§ 371 (c)(1),
(2) Date: May 27, 2021

(87) PCT Pub. No.: WO2020/108390
PCT Pub. Date: Jun. 4, 2020

(65) Prior Publication Data
US 2022/0097025 A1    Mar. 31, 2022

(30) Foreign Application Priority Data

Nov. 29, 2018  (CN) .......................... 201811485330.9

(51) Int. Cl.
*B01J 20/28*    (2006.01)
*B01D 15/08*    (2006.01)
(Continued)

(52) U.S. Cl.
CPC ........ *B01J 20/28047* (2013.01); *B01D 15/08* (2013.01); *B01D 36/045* (2013.01);
(Continued)

(58) Field of Classification Search
CPC ............... B01J 20/28047; B01J 20/261; B01J 20/28016; B01J 20/24; B01J 20/267;
(Continued)

(56) References Cited

U.S. PATENT DOCUMENTS

| | | |
|---|---|---|
| 4,555,344 A | 11/1985 | Cussler |
| 2005/0115890 A1 | 6/2005 | Demmer et al. |
| 2018/0320173 A1* | 11/2018 | Edelstein ............. C12Q 1/6876 |

FOREIGN PATENT DOCUMENTS

| | | |
|---|---|---|
| CN | 1153298 A | 7/1997 |
| CN | 102072836 A | 5/2011 |
| CN | 109569023 A | 4/2019 |

OTHER PUBLICATIONS

International Search Report issued in corresponding International application No. PCT/CN2019/120118, mailed Feb. 18, 2020.
(Continued)

*Primary Examiner* — Madeline Gonzalez
(74) *Attorney, Agent, or Firm* — JEEN IP LAW, LLC

(57) ABSTRACT

This invention belongs to the field of preparation of macromolecule sample of various volumes, pertaining to a detergent-mixed dry hydrogel particle and a method of using the particle to mass concentrate the macromolecule liquid sample or to enhance specific activity of the protein liquid sample. After thorough suspension and hydration in a detergent solution, the hydrogel particle is separated from the excess of the detergent solution and dried into the detergent-mixed dry hydrogel particle; upon contacting the macromolecule liquid sample in certain ratio with the dry particle having a pore size of its cross-linked network smaller than the macromolecule to allow absorption and swelling of the hydrogel particle, filter centrifugation or filter conical rotating drum centrifugation is exercised to remove the hydrogel particle whose surface is deprived of water and to collect the
(Continued)

concentrate filtrate of the macromolecule mass or the protein sample with enhanced specific activity.

9 Claims, 4 Drawing Sheets

(51) Int. Cl.
*B01D 36/04* (2006.01)
*B01D 63/16* (2006.01)
*B01J 20/26* (2006.01)
*C07K 1/36* (2006.01)
*C07K 14/765* (2006.01)
*C12N 9/08* (2006.01)
*C12N 9/16* (2006.01)

(52) U.S. Cl.
CPC ............ *B01D 63/16* (2013.01); *B01J 20/261* (2013.01); *B01J 20/28016* (2013.01); *C07K 1/36* (2013.01); *C07K 14/765* (2013.01); *C12N 9/0065* (2013.01); *C12N 9/16* (2013.01); *C12Y 111/01007* (2013.01); *C12Y 301/03001* (2013.01)

(58) Field of Classification Search
CPC ...... B01D 15/08; B01D 36/045; B01D 63/16; B01D 15/34; B01D 61/00; B01D 36/00; C07K 1/36; C07K 14/765; C07K 1/34; C12N 9/0065; C12N 9/16; C12Y 111/01007; C12Y 301/03001
USPC ... 210/360.1, 502.1, 500.1, 321.6, 644, 634, 210/635; 435/7.1
See application file for complete search history.

(56) References Cited

OTHER PUBLICATIONS

Written Opinion of the International Search Authority in corresponding International application No. PCT/CN2019/120118.
First Office Action from China Patent Office in a counterpart Chinese Patent Application 201811485330.9, Mailed Jan. 3, 2020.
Second Office Action from China Patent Office in a counterpart Chinese Patent Application 201811485330.9, Mailed Jul. 14, 2020.

* cited by examiner

DETERGENT-MIXED DRY HYDROGEL PARTICLE AND CONCENTRATION AND SPECIFIC ACTIVITY ENHANCEMENT OF MACROMOLECULE

TECHNICAL FIELD OF THE INVENTION

This invention relates to a detergent-mixed dry hydrogel particle and realization of a large fold of concentration of macromolecule with high recovery yield as well as enhancement of specific activity of protein.

BACKGROUND OF THE INVENTION

Macromolecule in this invention refers to natural biomacromolecule or assembly such as polysaccharide, nucleic acid, protein and their aggregate in their singular entity or combined entities as exemplified by ribosome, exosome, endosome, chromosome, organelle and virus, as well as synthetic soluble polymer or colloid such as polyacrylamide, polyacrylic acid, polyacrylate, polyvinyl alcohol, polyethylene glycol, polyvinyl pyrrolidone, latex particle and colloidal gold. In preparation, modification or analysis of these macromolecules, it is often necessary to concentrate them when they exist in a concentration too low. Although manipulation via organic solvent, acidity or basicity, ionic concentration, hydration competition agent or temperature is frequently used to induce precipitation and therefore concentration of macromolecule, the method suffers problems such as user-unfriendliness, low efficiency for a sample of low concentration and loss of active functionality of biomacromolecule. Comparatively speaking, ultrafiltration based on pressure and nano-porous membrane to concentration macromolecule enjoys advantages of gentleness and concentration efficiency being independent of sample concentration, while it comes with serious problems of slow process, membrane fouling, aggregation induced by the local concentration polarization on the membrane and conformational denaturation induced by the pressure for a protein sample.

We observe that, when a dry hydrogel particle hydrates and swells in a macromolecular solution, its cross-linked network structure allows spontaneous entry of water solvent and small molecule solute into the inner space of the network and at the same time exclusion of the macromolecule on the outside of the network, thus permitting concentration of the macromolecule in the space outside the network and collection of the concentrate upon convenient solid-liquid separation via simple filter centrifugation (Analytical Biochemistry, 1984, 138, 451). Because the surfaces of the hydrogel network which are evenly distributed throughout the whole liquid space are vastly larger than that of the single layer of the ultrafiltration membrane, concentration by this hydrogel largely avoids those problems of slowness, membrane blockage, protein aggregation from local concentration polarization of membrane and pressure-induced denaturation as encountered in the ultrafiltration concentration method. When conducting high-fold concentration, however, there is significant retention of the macromolecule concentrate on the surfaces of the swollen absorbent hydrogel particles which occupy a relatively high percentage of volume, resulting in serious reduction in recovery yield. Therefore, to execute concentration higher than 7-fold, for example, the thickness of hydrogel retained by the filter in the direction of the centrifugal force should not be too high, severely limiting the volume of macromolecule liquid sample to be concentrated through the filter centrifugal separation.

There are reports of mixing hydrogel and detergent for solidification or controlled release of detergent or fragrance while the mixture had not been disclosed in the prior art for the purpose of concentrating macromolecule until this invention now.

SUMMARY OF THE INVENTION

This invention provides a detergent-mixed hydrogel particle, a method of large-fold mass concentration of macromolecule liquid sample by the dry form of this hydrogel particle with high recovery yield, and a method of enhancing specific activity of protein liquid sample upon the concentration process. A measured amount of detergent-mixed dry hydrogel particle whose cross-linking forms a network of pore size smaller the size of the target macromolecule is allowed to contact with the macromolecule solution of varied volumes to be concentrated, resulting in concentrate outside the network through absorption of the liquid and any small molecule solute by the swelling hydrogel inside the cross-linked network and exclusion of the macromolecule outside the cross-linked network; separation on the mixture of the hydrogel particle and the macromolecule liquid solution is then carried out by filter centrifugation or conical drum centrifugation; upon removal of the internally swollen absorbent porous hydrogel particle whose surface is deprived of water, the filtrate is obtained as the concentrate of the target macromolecule which is excluded outside the hydrogel. If the macromolecule is protein, the concentration process described above also enhances the protein's specific activity and thus services as a method to enhance specific activity of protein. This invention overcomes the shortcomings of the current macromolecule concentration techniques such as user-unfriendliness, slowness, blockage, low efficiency of local concentration, polarization and loss of functional activity.

DETAILED DESCRIPTION OF THE INVENTION

Figure 1:
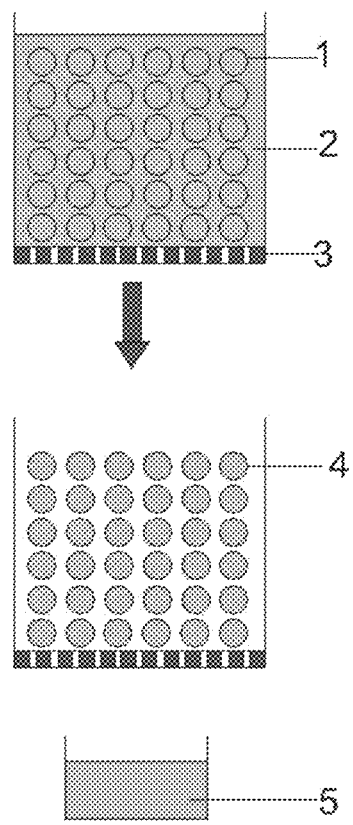
FIG. 1 illustrates separation on the mixture of the swollen absorbent hydrogel particle and the macromolecule concentrate via filter centrifugation.

Alternate combination of over 20 amino acid monomers results in proteins of enormous diversity in primary sequence and its derivative conformations. Although these conformations are mostly required as a structural basis to fulfill the active function of protein, they are often unstable and thus prone to change and corresponding loss of the active functionality upon action of time, physical factors and chemical influences, making a phenomenon called denaturation.

Hydrogel forms three-dimensional polymeric network cross-linked by chemical covalent bonding or physical non-covalent bonding with hydrophilic groups to contain water solvent or solution within this network. Common examples of natural or man-made hydrogel include, but are not limited to, polyacrylamide, polyacrylic acid, polyacrylate, polydextran, cellulose, polyvinyl alcohol, polyethylene glycol, agarose, polyhyaluronic acid, polychitosan, polyalginic acid, polyalginate sodium, polyvinyl pyrrolidone, polypeptide, ployprotein, modified hydrogel polymerized and cross-linked with a modified version of one of the above-mentioned monomers, or hybrid hydrogel polymerized and cross-linked with combination of at least two members of the above-mentioned monomers and the above-mentioned hydrogels.

Homogeneous single-phase bulk hydrogel can be made via polymerization and cross-linking of a monomer solution or cross-linking of a polymer solution, and processed into particles through steps of cutting, washing, drying and grinding; if the above-mentioned hydrogel is unable to absorb all water, it emerges as a separate phase from the solution and can be turned into particles through a process of washing, drying and grinding if needed; hydrogel particles can also be made directly through polymerization and cross-linking of monomer or cross-linking of polymer in form of dispersed suspension droplets, followed by steps of washing and drying. As a preferred method to mix in detergent, the above-mentioned hydrogel particles can all finally be fully hydrated, swollen and suspended in a detergent solution of certain mixing concentration, be separated from the excess solution preferably via filtration, and be dried into the detergent-mixed dry hydrogel particle of this invention. Ranked roughly by degree of friendliness toward active functionality of protein, detergents common in field of biological sciences include, but are not limited to, Tween-20, Tween-40, Tween-60, Tween-80, Brij-35, Brij-58, NP-40, Triton X-100, Triton X-114, octyl glucopyranoside, octyl thioglucoside, 3-[(3-cholamidopropyl) dimethylammonio]-1-propanesulfonate, 3-[(3-cholamidopropyl)dimethylammonio]-2-hydroxy-1-propanesulfonate, sodium cholate, sodium deoxycholate, hexadecyl trimethyl ammonium bromide, and sodium dodecyl sulfate.

It can be imagined that, when the above-mentioned dry hydrogel particle in measured quantity proportional to the volume of the macromolecule aqueous solution to be concentrated is added into the solution, the hydrophilic groups of the cross-linked network with vast surface area guides in and sucks in the aqueous solution, and releases the torsion tension of the network which is filled by the solution to reverse its originally collapsed state resulting from the particle's drying process. Therefore, uptake of the aqueous solution by the steric network space of the dry hydrogel particle is a rapid and spontaneous event with no need of energy input. If the pore size of the cross-linked network is smaller than the size of the target macromolecule, the macromolecule is excluded and forms concentrate along with the liquid outside the network. As the detergent is first mixed with the hydrogel particle in liquid, it can exist in a state of monomer or micell inside or outside the network of the hydrogel and should remain in a certain amount of liquid inside the network and on the outside surface of the network after removal of the bulk excess liquid and drying the hydrogel particle. When such detergent-mixed dry hydrogel particle absorbs aqueous liquid to concentrate macromolecule, there is a sufficiently high local concentration of the detergent on the surface of the particle network which effectively reduces adsorption of the macromolecule on the particle's surface and equally effectively diminishes the surface tension of the concentrate liquid outside the network to facilitate its efficient phase separation in mutually opposite direction with the particle under driving force of the filter centrifugation described below. Therefore, the mixing of the detergent with the hydrogel particle enhances the recovery yield of the overall macromolecule solute mass by collecting more solute mass and liquid volume of the macromolecule in the concentrate. It should be noted that if there is a loss of the detergent outside the hydrogel network due to its interaction with the target macromolecule or its diffusion into the concentrate, the detergent originally inside the network can diffuse out to replenish the loss of the detergent and maintain its function of enhancing recovery yield of the target macromolecule. When a large fold of concentration over a large volume of macromolecule liquid sample is carried out, a thick layer of the swollen absorbent hydrogel particle is formed in the direction of the centrifugal force in the filter centrifugal separation process described below to recover the concentrate of small volume percentage, especially highlighting prominent and important role of the mixing of the detergent and dry hydrogel particle for high recovery yield of the overall solute mass of the macromolecule concentrate.

Imaginably, protein in aqueous liquid often exists in tightly folded, reversibly loose intermediate and irreversibly loose conformations in correspondence with active, reversibly inactive and irreversibly inactive functional conformational states, respectively. When a protein liquid sample is subject to the concentration process with the dry hydrogel particle in mix with a detergent friendly to the protein's active functionality as described above, it can be imagined that the hydrating water molecules surrounding the protein's surface is sucked away quickly that the reversibly loose intermediate conformation contracts back to its tightly folded conformation due to the loss of its hydration, thus restoring its inactive functional conformation back to an active functional conformational state and enhancing the total and specific activity of the protein liquid sample, or in other words purifying or enriching the active functional conformation of the protein sample. The enhancement, as opposite to diminishment, in active function of a protein liquid sample through the concentration process with the dry hydrogel particle is a beneficial sample processing, while the enhanced conformational purity in addition to compositional purity helps protein's crystallization which requires cooperative lining of molecules of homogeneity in both compositional and conformational aspects and facilitates various protein's structural analysis which appreciates conformational homogeneity.

Filter centrifugation is a well-established method to efficiently separate a mixture of solid and liquid and recover the liquid with a high yield, thus well meeting the need of separating the small amount of the concentrate from the large amount of the hydrogel particle in the high-fold concentration process of macromolecule described above. Conventional laboratory or industrial filter centrifuges can all be used in this invention. As illustrated in FIG. 1, in a rotating container, the swollen absorbent hydrogel particle 1 and the macromolecule concentrate 2 in a mixture as described above all move toward the filter membrane 3 containing a proper pore size under the direction of centrifugal force indicated by the arrow, upon action of appropriate centrifugal strength and time retaining the hydrogel particle 4 on the filter whose particulate surface is deprived of water and throwing out the concentrate 5 for collection with high efficiency.

Figure 2:
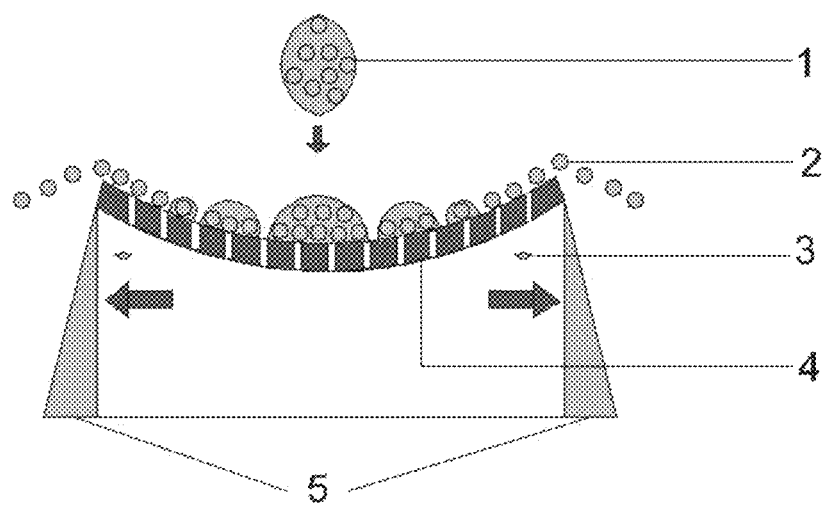
FIG. 2 illustrates continuous separation on a large volume of macromolecule liquid sample to be concentrated via filter centrifugation.

To concentrate a large volume of macromolecule liquid sample in an industrial scale, technologically well-developed continuous centrifugal system to separate a solid-liquid mixture can be employed where continuous removal of the swollen absorbent hydrogel particle accumulated on the filter avoids the retention and loss of the concentrate and the target macromolecule which would be otherwise caused by non-stopped accumulation of the hydrogel particle, while collecting the concentrate at the same time. A preferred simple continuous operating system is illustrated in FIG. 2, featuring the key component of a conical rotating drum containing filter pores. While the drum rotates, the mixture 1 of the swollen absorbent hydrogel particles and the macromolecule concentrate is continuously fed onto the bottom of small diameter; upon action of the centrifugal force in the direction indicated by the arrow, the hydrogel particles 2 which are retained on the filter and deprived of water on their particulate surfaces continuously move upward along the wall of larger diameters and are eventually thrown out; meanwhile the concentrate 3 is continuously pushed out of the filter 4 to be collected as the concentrate 5. The process described above constitutes a continuous operation to concentrate a large volume of macromolecule liquid sample which comprises feeding, removal of hydrogel particles deprived of surface-associated water and collection of concentrate.

Figure 3:
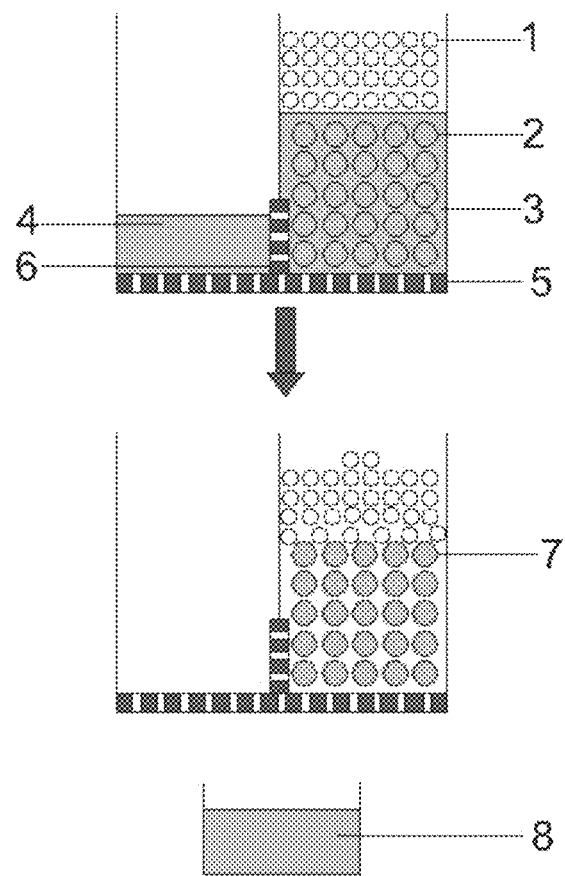
FIG. 3 illustrates contact and rate-controlled liquid absorption with two spatially separated regions for macromolecule liquid sample and dry hydrogel particle.

The fold of concentration of macromolecule as mentioned above is controlled by the ratio of the mass of the dry hydrogel particle over the volume of the liquid sample to be concentrated, with more use of the hydrogel relative to the liquid to achieve a higher fold of concentration. To achieve a certain fold of concentration, a liquid sample of macromolecule of various volumes requires input of the dry hydrogel particle with various correspondingly measured masses. If a small volume of macromolecule liquid sample is to be concentrated, measurement of a small quantity of dry hydrogel particle is inconvenient, with too little particle resulting in insufficient concentration or too much particle drying up the liquid sample and recovering nothing. Therefore, this invention constructs a contact and liquid absorption system with spatial separation of dry hydrogel particle in excess relative to macromolecule liquid sample to be concentrated, as illustrated in FIG. 3. On one side of the system there is a region of excess dry hydrogel particle which comprises the still-dry hydrogel particle 1, the swollen absorbent hydrogel particle 2 and the macromolecule concentrate 3; the other side of the system is used as a sample entry region to receive the macromolecule liquid sample 4; the filter membrane 5 on the bottom of the system serves to retain both swollen absorbent and non-swollen non-absorbent hydrogel particles; the macromolecule liquid sample and excess dry hydrogel particle in the two separate regions contact one another on the contact membrane 6 on the bottom of the system, effecting absorption of the liquid upon its migration from the left to the right as driven by the capillary suction. There should be proper design of the size and density of the pores of the contact membrane 6 to prevent too much hydrogel particle getting into the sample entry region, while the macromolecule liquid sample 4 can easily run through into the excess dry hydrogel particle region and yet not too quickly to be efficiently recovered before being totally sucked up and absorbed dry. In operation, the whole concentration system is subject to centrifugation force in direction as indicated by the arrow immediately after the macromolecule liquid sample 4 is sucked and contracted to a desirable level, retaining the swollen absorbent hydrogel particle 7 on the filter whose surface is deprived of water while passing the concentrate 8 through the filter for collection. It should be noted that while there could be part of the macromolecule concentrate 3 passing through the contact membrane 6 into the sample entry region to mix with the macromolecule liquid sample 4 this mixture is ultimately collected into the concentrate 8 by centrifugation, ensuring overall high recovery yield of the macromolecule.

The substantive content of this invention is disclosed in, but is not limited to, the following examples. Unless specified in detail, the raw materials, equipment and methods in the examples can be obtained from normal commercial venues, published literature or the prior art.

Example 1: Optimization

Type of hydrogel particle: Selection on the type of hydrogel particle may be based on ease of preparation, cost of manufacturing and nature of interaction with target macromolecule. Polyacrylamide and polydextran are preferred hydrogels because of their advantages in relative ease and low cost in manufacturing and inert nature in interaction with macromolecule; hydrogel made from polyacrylic acid or polyacrylate is preferred because of its very large capacity in liquid absorption per unit mass in addition to its ease and low cost in manufacturing, although close attention should be paid to the impacts on the concentration protocol and recovery yield by the interaction of its negative charges with target macromolecule.

Type and concentration of mixing detergent: Concentration of the detergent to be mixed with the hydrogel for the highest recovery yields of mass and active functionality of target macromolecule based on its interaction with the hydrogel is selected from a range of 0.001~10%.

For sensitive biomacromolecule other than polysaccharide and nucleic acid, such as protein and especially enzyme whose active functionality is very sensitive to its conformation, nonionic mixing detergents such as Tween series, Brij series, NP-40 and Triton series are preferred; Tween series are especially preferred as they do not effect negative impacts on active functionality of most biomacromolecules while often preventing aggregation of these macromolecules and corresponding loss of their active functionality.

Pore size of cross-linked network of hydrogel: This size is usually positively related to concentration of monomer or polymer and degree of the cross-linking in preparation of the hydrogel, while it should be smaller than size of target macromolecule; the size of the target macromolecule is usually in positive relationship with factors such as its molecular weight, its conformational looseness determined by arrangement of its residue groups and its thickness of hydration layer, however.

Size of hydrogel particle: The particle size being too small results in a larger surface area to more easily attract the target macromolecule and retain the macromolecule concentrate, and demands a reduced size of filter pore to decrease rate and efficiency of the filtration; the particle size being too large slows down its absorption and swelling. The preferred size of dry or swollen absorbent hydrogel particle ranges 1~5000 micrometer, while the size ranging 5~1000 micrometer is further preferred.

Pore size and material of filter membrane in filter centrifugation: This pore should be small enough to retain the dry or swollen absorbent hydrogel particle. If this size is too small, however, filtration may be too slow; if this size is too big, it may not be able to hold the mixture of the macromolecule concentrate and the swollen absorbent hydrogel before centrifugation, because there is a moment for a need to prevent the concentrate from leaking out of the filter pore which is overly too large. Thus, the preferred pore size ranges 0.5~1000 micrometer. The filter membrane should not absorb macromolecule, although it can be either hydrophilic or hydrophobic. Generally speaking, a filter membrane with small pore is preferably matched with hydrophilic filter surface to facilitate passage of liquid driven by the centrifugal force, while a big filter pore preferably works with the liquid-repelling hydrophobic filter material to hold the liquid sample with no leakage before the filter centrifugation.

Example 2: Preparation of Detergent-Mixed Dry Polyacrylamide Hydrogel Particle Using Method of Single-Phase Polymerization Components: acrylamide 29 grams, N,N'-methylenebisacrylamide 1 gram, deionized water 100 milliliters, ammonium persulphate 0.2 gram, N,N,N',N'-tetramethylethylenediamine 40 microliters.

Procedure: The solids of acrylamide, N,N'-methylenebisacrylamide and ammonium persulphate are dissolved in the deionized water in a beaker and stirred for a homogenous solution, followed by addition of N,N,N',N'-tetramethylethylenediamine to initiate polymerization before being immediately poured onto a container of large bottom area and inert inner surfaces to sit still for 1 hour for complete polymerization; the gel is cut into pierces and dried at 90° C.; the dry gel pieces are ground with a grinder for sieving out those particles meshed 60~150 for full swelling with deionized water; the particles are washed twice with 250 milliliters of deionized water, and twice again with 250 milliliters of Tween-20 solution at a concentration preferably 0.01~1%, especially preferably 0.2%; the resultant wet particles are dried at 90° C. and stored sealed.

Example 3: Preparation of Detergent-Mixed Dry Polyacrylamide Hydrogel Particle Using Method of Reverse-Phase Suspension Polymerization Water phase composition: a homogenous solution of 29 grams of acrylamide, 1 gram of N, N'-methylenebisacrylamide, 100 milliliters of deionized water and 0.2 gram of ammonium persulphate. Oil phase composition: a homogenous mixture of 200 milliliters of cyclohexane and 3 milliliters of Span-80.

Procedure: The oil phase prepared in a three-neck flask equipped with a mechanical stirrer and an Allihn condenser is heated to 57° C. under stirring of 240 revolutions per minute; a mixture is formed by adding the water phase prepared in a beaker into the oil phase in the flask, dispersing the water phase into the oil phase under stirring at 57° C. over 30 minutes; heated to 67° C., the system releases heat, produces much reflux, and is further incubated for 30 minutes after all the heat is released; the temperature is raised to 70° C. and kept for 30 minutes; cyclohexane is removed under vacuum filtration with a Buchner funnel after the reaction is completed; the solid retained is washed with 250 milliliters of 50% ethanol for 3 times, again 250 milliliters of deionized water for 3 times; washing of 2 times with 250 milliliters of Tween-20 solution at a concentration preferably ranging 0.01~1%, especially preferably 0.2%, is carried out; the resultant wet particles are dried at 90° C. and stored sealed.

Example 4: Concentration Bovine Serum Albumin Protein

Figure 4:
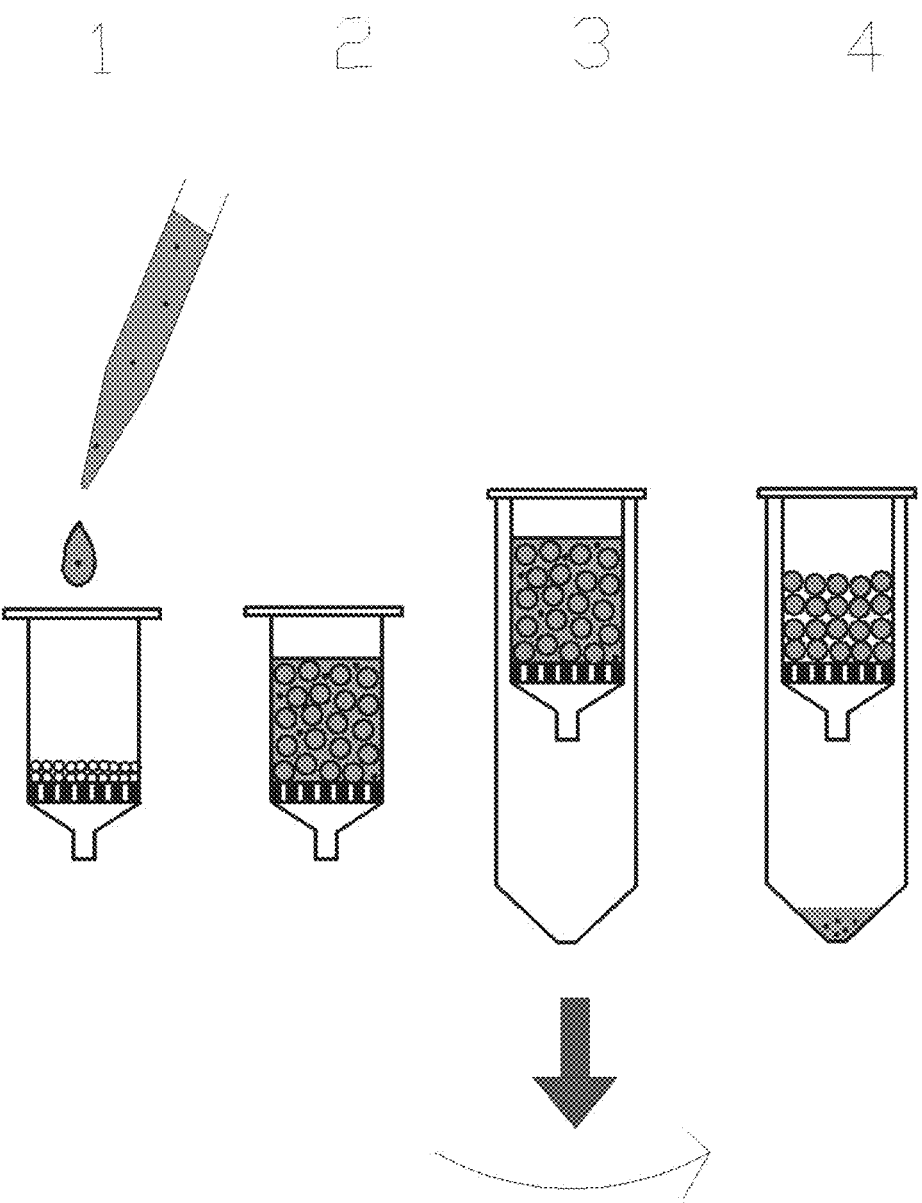
FIG. 4 illustrates method to concentrate macromolecule by horizontal rotor filter centrifugation.

As illustrated in FIG. 4, in the first step, 2 grams of the detergent-mixed dry polyacrylamide hydrogel particle prepared as described in Example 2 or 3 are weighted and added into a plastic tube with a filer membrane of pore size of 20 micrometers and a protruding adaptor on the top opening, followed by addition of 12 milliliters of bovine serum albumin protein (black dots in the figure) solution at a concentration ranging 10~500 micrograms per milliliter in phosphate-buffered saline pH7.4; in the second step, the mixture of the hydrogel and the protein solution is stilly incubated for 5 minutes to allow full hydration, absorption and swelling; in the third step, the above-mentioned plastic tube adapts onto a 50-milliliter centrifuge tube, and is spun 3000×g for 3 minutes in the circular direction indicated by the narrow arrow with horizontal centrifugation; in the fourth step, about 2 milliliters of the bovine serum albumin concentrate is collected in the direction of centrifugal force indicated by the coarse arrow of the tube set. The mass recovery yield of the protein concentrate is determined to be higher than 90%, while the concentration is enhanced by about 6 folds compared to the initial value.

Example 5: Desalting and Buffer Exchange of Bovine Serum Albumin Protein Solution The bovine serum albumin protein concentrate obtained in Example 4 is mixed with 10 milliliters of deionized water, and then 2 grams of the detergent-mixed dry polyacrylamide hydrogel particle prepared as described in Example 2 or 3 in the filter membrane plastic tube; repeating the operation of still hydration and centrifugal separation described in Example 4 results in 2 milliliters of concentrate. This concentrate is 83% less in salt and buffer strength than the concentrate obtained in Example 4. Repeating the desalting and buffer exchange operation described above one more time enhances the efficiencies of desalting and buffer exchange to be about 97%.

Example 6: Enhancement of Specific Activity of Alkaline Phosphatase

The procedure of Example 4 to concentrate 12 milliliters of sample volume is followed with calf intestinal alkaline phosphatase solution at a concentration ranging 20~200 micrograms per milliliter in tris (hydroxymethyl)aminomethane buffer pH7.5, rather than the bovine serum albumin solution in the example. The recovery yields of the protein mass and the alkaline phosphatase enzymatic activity of the resultant concentrate are determined to be 90% and 100%, respectively, thus indicating a 11% enhancement of the specific activity of the alkaline phosphatase.

Example 7: Concentration of Protein in Urine

Protein of trace amounts in human urine can be concentrated to enhance its concentration and detectability. Horseradish peroxidase as a model protein is spiked into normal human urine at a concentration of 2 micrograms per milliliter. The procedure of Example 4 to concentrate 12 milliliters of sample volume is followed with the model protein urine sample, rather than the bovine serum albumin solution in the example. The fold of concentration and the recovery yield of the enzyme protein concentrate are about 6 and higher than 95%, respectively, as determined by the horseradish peroxidase activity assay.

Example 8: Concentration of M13 Phage Secreted into Culture Medium

There is a need to concentrate M13 phage assembled in *Escherichia coli* and secreted into culture medium for screening target phage to serve in sequencing or phage display. The current method of concentrating M13 phase based on polyethylene glycol precipitation suffers low recovery yield over a large volume of culture medium or a low titer, in addition to operational requirements of low temperature and long time. As an improved method, the procedure of Example 4 of this invention to concentrate 12 milliliters of sample volume is followed with the M13 phage secrete sample in culture medium, rather than the bovine serum albumin solution in the example. The fold of concentration and the recovery yield of the M13 phage concentrate are about 6 and 95%, respectively, as finally determined by titer assay.

The invention claimed is:

1. A detergent-mixed dry hydrogel particle for mass concentrating of macromolecule or enhancing specific activity of protein, comprising: hydrogels and detergent;
   wherein the pore size of the detergent-mixed dry hydrogel particle's cross-linked network is smaller than the size of the macromolecule;
   wherein a portion of the detergent is located at an inside of the network, and another portion of the detergent is located at an outside surface of the network of the dry hydrogel particle;
   the another portion of the detergent located at the outside surface of the network is configured to reduce adsorption of the macromolecule to the surface of the network; and
   the portion of the detergent located at the inside of the network is configured to, when the another portion of the detergent located at the outside surface of the network is lost, diffuse out to reach the outside surface of the network for replenishing loss of the another portion of the detergent.

2. The detergent-mixed dry hydrogel particle according to claim 1, wherein the hydrogels are selected from the group consisting of polyacrylamide, polyacrylic acid, polyacrylate, polydextran, cellulose, polyvinyl alcohol, polyethylene glycol, agarose, polyhyaluronic acid, polychitosan, polyalginic acid, polyalginate sodium, polyvinyl pyrrolidone, polypeptide, polyprotein, modified hydrogel polymerized and crosslinked with a modified version of one of the above-mentioned monomers, or hybrid hydrogel polymerized and cross-linked with combination of at least two members of the above-mentioned monomers and the above-mentioned hydrogels.

3. The detergent-mixed dry hydrogel particle according to claim 1, wherein the detergent is selected from the group consisting of Tween-20, Tween-40, Tween-60, Tween-80, Brij-35, Brij-58, NP-40, Triton X-100, Triton X-114, octyl glucopyranoside, octyl thioglucoside, 3-[(3-cholamidopropyl) dimethylammonio]-1-propanesulfonate, 3-[(3-cholamidopropyl) dimethylammonio]-2-hydroxy-1-propanesulfonate, sodium cholate, sodium deoxycholate, hexadecyl trimethyl ammonium bromide, and sodium dodecyl sulfate.

4. The detergent-mixed dry hydrogel particle according to claim 1, wherein the detergent is mixed at a concentration ranging 0.001~10%.

5. A method to mass concentrate macromolecule, comprising steps of 1) contacting the detergent-mixed dry hydrogel particle according to claim 1 with a macromolecule liquid sample at a certain ratio of the particle mass and a liquid volume and allowing the detergent-mixed dry hydrogel particle to absorb and swell and to exclude out the macromolecule; 2) subjecting the mixture of the macromolecule liquid sample and the detergent-mixed dry hydrogel particle to filter centrifugal separation; and 3) collecting a macromolecule concentrate filtrate excluded by the detergent-mixed dry hydrogel particle upon filter removal of the particle whose surface is deprived of water and whose inner space absorbs and swells.

6. The method according to claim 5, wherein the filter centrifugal separation is continuously operated with a conical filter rotating drum comprising a) continuous feeding of the mixture of the macromolecule liquid sample and the detergent-mixed dry hydrogel particle onto the bottom of the drum of smaller diameter; b) the particle whose surface is deprived of water and whose inner space absorb and swells being thrown upward continuously toward the upper part of the drum of larger diameter under the centrifugal force; and c) the macromolecule concentrate filtrate being continuously spun through a filter membrane for collection.

7. The method according to claim 5, wherein the speed and extent of the absorption of the liquid of the macromolecule liquid sample by the particle are controlled by a contact membrane separating the macromolecule liquid sample and the excess amount of the particle into two regions.

8. A method to enhance specific activity of protein, comprising steps of 1) contacting the detergent-mixed dry hydrogel particle according to claim 1 with a protein liquid sample at a certain ratio of the particle mass and a liquid volume and allowing the detergent-mixed dry hydrogel particle to absorb and swell and to exclude out the protein; 2) subjecting the mixture of the protein liquid sample and the detergent-mixed dry hydrogel particle to filter centrifugal separation; and 3) collecting a protein concentrate filtrate excluded by the detergent-mixed dry hydrogel particle upon filter removal of the detergent-mixed dry hydrogel particle whose surface is deprived of water and whose inner space absorbs and swells.

9. A method to process a protein liquid sample for crystallization or conformational analysis, comprising steps of 1) contacting the detergent-mixed dry hydrogel particle according to claim 1 with a protein liquid sample at a certain ratio of the particle mass and a liquid volume and allowing the detergent-mixed dry hydrogel particle to absorb and swell and to exclude out the protein; 2) subjecting the mixture of the protein liquid sample and the detergent-mixed dry hydrogel particle to filter centrifugal separation; and 3) collecting a protein concentrate filtrate excluded by the detergent-mixed dry hydrogel particle upon filter removal of the detergent-mixed dry hydrogel particle whose surface is deprived of water and whose inner space absorbs and swells.

* * * * *